(12) United States Patent
Whiseant et al.

(10) Patent No.: US 10,207,078 B2
(45) Date of Patent: Feb. 19, 2019

(54) STEERABLE INTRAVASCULAR DEVICES AND ASSOCIATED DEVICES, SYSTEMS, AND METHODS

(71) Applicant: Volcano Corporation, San Diego, CA (US)

(72) Inventors: Chester Whiseant, Marysville, CA (US); Richard Dunn, Rancho Cordova, CA (US)

(73) Assignee: Volcano Corporation, San Diego, CA (US)

( * ) Notice: Subject to any disclaimer, the term of this patent is extended or adjusted under 35 U.S.C. 154(b) by 1107 days.

(21) Appl. No.: 14/135,310

(22) Filed: Dec. 19, 2013

(65) Prior Publication Data

US 2014/0180124 A1 Jun. 26, 2014

Related U.S. Application Data

(60) Provisional application No. 61/745,512, filed on Dec. 21, 2012.

(51) Int. Cl.
*A61B 5/0215* (2006.01)
*A61M 25/01* (2006.01)
(Continued)

(52) U.S. Cl.
CPC ..... *A61M 25/0147* (2013.01); *A61B 5/02055* (2013.01); *A61B 5/6852* (2013.01);
(Continued)

(58) Field of Classification Search
CPC combination set(s) only.
See application file for complete search history.

(56) References Cited

U.S. PATENT DOCUMENTS 5,368,564 A 11/1994 Savage
5,954,654 A * 9/1999 Eaton ................ A61B 1/0052
600/459

(Continued)

FOREIGN PATENT DOCUMENTS

JP 7059863 A 3/1995
JP 9084878 A 3/1997
(Continued)

OTHER PUBLICATIONS

International Searching Authority/European Patent Office, Communication—Supplementary European Search Report, for European Application No. 13865822.4, dated Oct. 12, 2016, 11 pages.
(Continued)

*Primary Examiner* — Christopher Cook

(57) ABSTRACT

A steerable sheath for a catheter delivery system and associated devices and methods are disclosed. In some embodiments, the catheter delivery system includes a catheter sheath having a steerable distal portion and a flexible elongate member connecting to a steering unit. The flexible elongate member has a central lumen through which a therapeutic or diagnostic device of a first modality can be inserted, used to perform a procedure, and then removed and replaced by a different therapeutic or diagnostic device while the catheter sheath remains substantially at the same location within a patient.

30 Claims, 7 Drawing Sheets

(51) Int. Cl.
    *A61B 5/00*         (2006.01)
    *A61B 8/12*         (2006.01)
    *A61B 5/0205*     (2006.01)
    *A61B 8/08*         (2006.01)
    *A61B 8/00*         (2006.01)
    *A61B 5/026*      (2006.01)

(52) U.S. Cl.
    CPC .......... *A61B 8/0883* (2013.01); *A61B 8/0891* (2013.01); *A61B 8/12* (2013.01); *A61B 8/445* (2013.01); *A61B 5/026* (2013.01); *A61B 5/0215* (2013.01); *A61M 25/0136* (2013.01)

(56) References Cited

U.S. PATENT DOCUMENTS

| | | | |
|---|---|---|---|
| 6,010,449 | A | 1/2000 | Selmon et al. |
| 7,553,323 | B1 | 6/2009 | Perez et al. |
| 2004/0181140 | A1 | 9/2004 | Falwel et al. |
| 2004/0193016 | A1 | 9/2004 | Root et al. |
| 2005/0272975 | A1 | 12/2005 | McWeeney et al. |
| 2007/0276324 | A1 | 11/2007 | Laduca et al. |
| 2008/0009745 | A1 | 1/2008 | Hossack et al. |
| 2008/0161798 | A1* | 7/2008 | Podmore .......... A61B 17/00234 606/41 |
| 2008/0287862 | A1* | 11/2008 | Weitzner .......... A61M 25/0136 604/28 |
| 2009/0024110 | A1* | 1/2009 | Heideman .......... A61M 25/0012 604/528 |
| 2010/0004633 | A1 | 1/2010 | Rothe et al. |
| 2010/0179383 | A1* | 7/2010 | Motai .................. A61B 1/0051 600/106 |
| 2010/0331820 | A1* | 12/2010 | Prisco .................. A61B 1/0052 604/528 |
| 2013/0096572 | A1* | 4/2013 | Donhowe .............. A61B 34/10 606/130 |

FOREIGN PATENT DOCUMENTS

| | | |
|---|---|---|
| JP | 2001008939 A | 1/2001 |
| JP | 2003088527 A | 3/2003 |

OTHER PUBLICATIONS

International Search Report and Written Opinion received in corresponding Patent Cooperation Treaty Application No. PCT/US2013/075732, dated Apr. 3, 2014, 17 pages.

International Searching Authority/European Patent Office, "Communication—Supplementary Partial European Search Report," for European Application No. 13865822.4, dated Jul. 6, 2016, 5 pages.

* cited by examiner

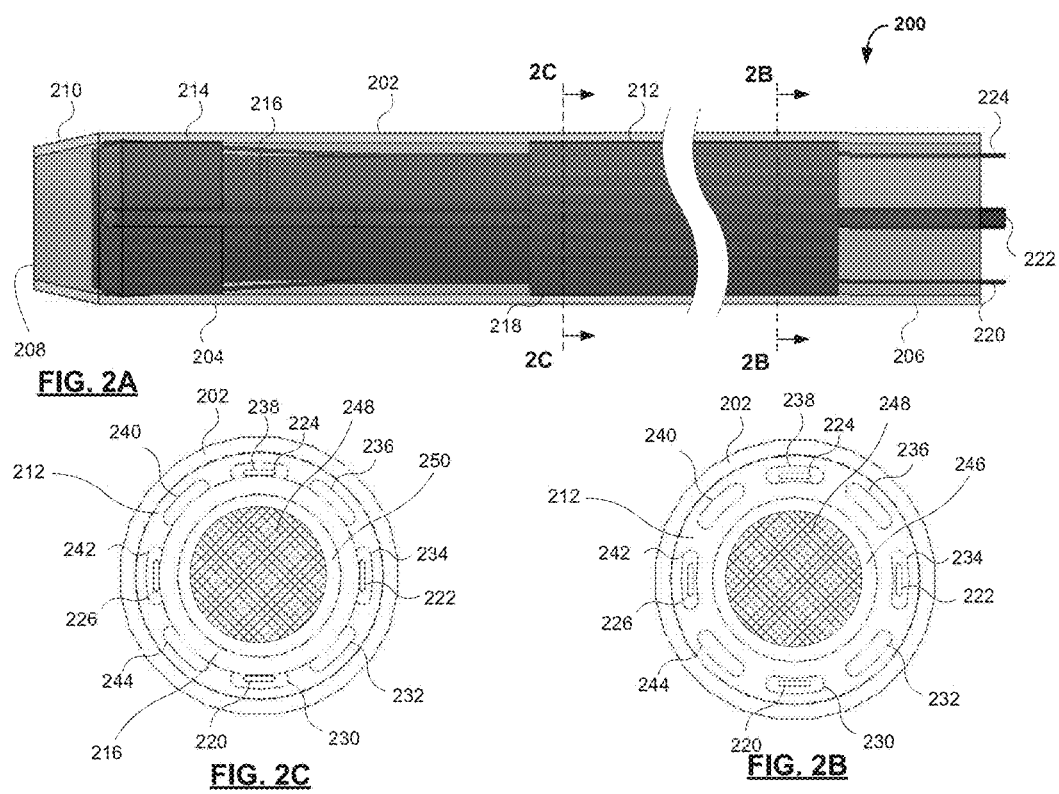

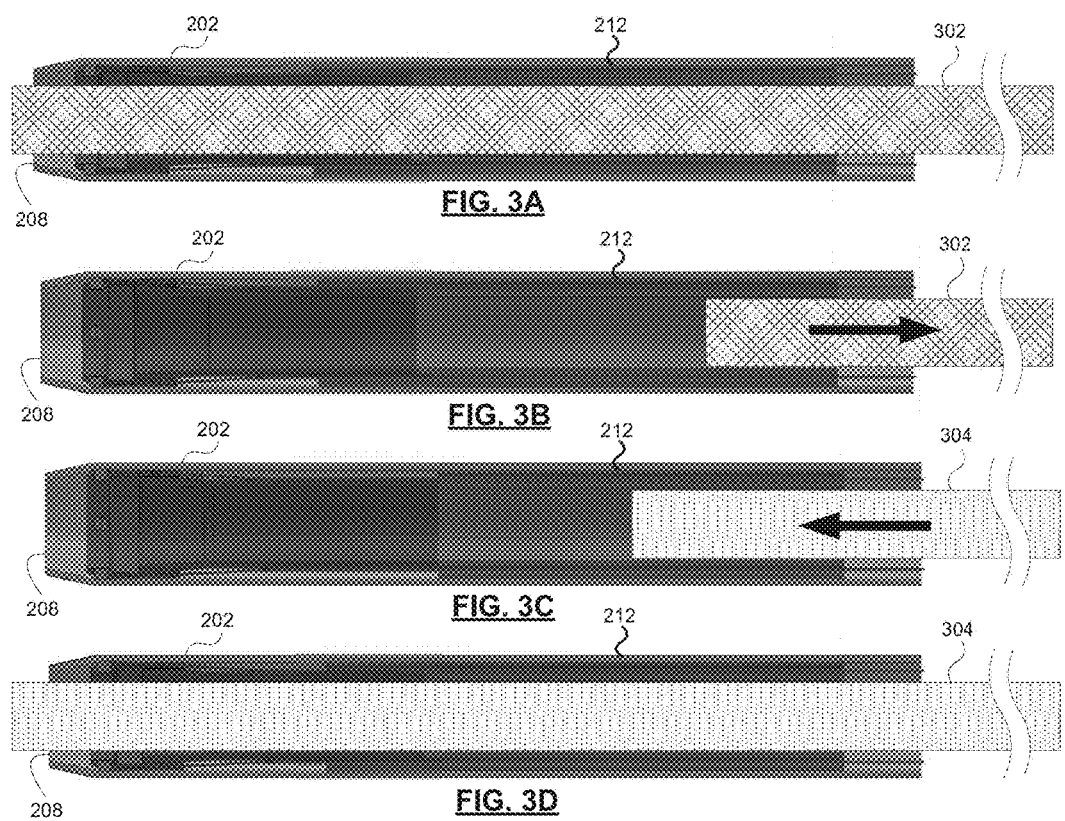

STEERABLE INTRAVASCULAR DEVICES AND ASSOCIATED DEVICES, SYSTEMS, AND METHODS

CROSS-REFERENCE TO RELATED APPLICATIONS

The present application claims priority to and the benefit of U.S. Provisional Patent Application No. 61/745,512, filed Dec. 21, 2012, which is hereby incorporated by reference in its entirety.

TECHNICAL FIELD

The present disclosure is related to intravascular devices and associated systems as used in the diagnosis and treatment of various maladies. In particular, embodiments disclosed herein are particularly suited for use in intravascular and intracardiac imaging and treatment devices.

BACKGROUND

Heart disease is one of many serious conditions that can require emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Surgeons may rely on a variety of modalities to observe and characterize a condition in order to determine the best course of treatment. Other conditions also necessitate investigations within a patient's body. Techniques such as X-ray fluoroscopy, fractional flow reserve (FFR), intravascular ultrasound (IVUS), optical coherence tomography (OCT), and other modalities are used to gather many different kinds of data to provide for a thorough assessment of a patient.

Some of these techniques utilize intravascular catheters and/or guidewires. Often intravascular catheters and guidewires are utilized to measure the pressure within the blood vessel (e.g., to calculate FFR), visualize the inner lumen of the blood vessel (e.g., IVUS, OCT, etc.), and/or otherwise obtain data related to the blood vessel. Such catheters and guidewires contain pressure sensors, imaging elements, and/or other electronic, optical, or electro-optical components. While these systems enable the collection of various types of data, the use of multiple diagnostic and/or therapeutic modalities during a single procedure has not traditionally been used because of the complexity, time, and increased risks to the patient.

Accordingly, there remains a need for improved intravascular devices, systems, and methods for guiding one or more electronic, optical, or electro-optical components to target locations within a patient.

SUMMARY

In one exemplary aspect, the present disclosure is directed to a method for directing multiple intravascular devices to a region of interest within a vessel of a patient. The method includes inserting a catheter sheath into the patient and guiding a distal portion of the catheter sheath to the region of interest utilizing a steering actuator coupled to a proximal portion of the catheter sheath. The method also includes performing a first procedure at the region of interest with a first intravascular device at least partially received within the distal portion of the catheter sheath. Further, the method includes performing a second procedure at the region of interest with a second intravascular device at least partially received within the distal portion of the catheter sheath. The second procedure is of a different modality than the first procedure.

In another exemplary aspect, the present disclosure is directed to a catheter delivery system. The catheter delivery system includes a catheter sheath that has a steerable distal portion and a plurality of steering lines running through a plurality of peripheral lumens of a first flexible elongate member having a central lumen. The distal ends of the plurality of steering lines are connected to a steering ring in the steerable distal portion of the catheter sheath and the proximal ends of the plurality of steering lines are connected to a steering actuator coupled to a housing sized and shaped for handheld use. The housing includes an opening extending therethrough in communication with the central lumen of the first flexible elongate member to allow the insertion of intravascular devices of different modalities into the central lumen of the first flexible elongate member, and also to allow removal of the intravascular devices of different modalities from the central lumen.

In yet another exemplary aspect, the present disclosure is directed to another catheter delivery system. The catheter delivery system includes a housing that has a joystick and a catheter sheath. The catheter sheath has a steerable distal portion and a plurality of steering lines plurality of steering lines being connected to the joystick at a proximal end and a steering ring at a distal end. The steering ring is positioned within the steerable distal portion of the catheter sheath.

These and other embodiments will be described in further detail below with respect to the following figures.

BRIEF DESCRIPTION OF THE DRAWINGS

Illustrative embodiments of the present disclosure will be described with reference to the accompanying drawings, of which:

FIG. 2A is a diagrammatic cut-away side view of a portion of a catheter sheath device according to an embodiment of the present disclosure.

FIG. 2B presents a cross-sectional end view of the catheter sheath device of FIG. 2A taken along line 2B-2B of FIG. 2A.

FIG. 2C presents a cross-sectional end view of the catheter sheath device of FIG. 2A taken along line 2C-2C of FIG. 2A.

FIG. 3A is a cross-sectional side view of a catheter sheath device with an intravascular device fully received therein.

FIG. 3B is a cross-sectional side view of the catheter sheath device of FIG. 3A, but showing the intravascular device being removed from the catheter sheath device.

FIG. 3C is a cross-sectional side view of the catheter sheath device of FIG. 3A, but with a different intravascular device being inserted into the catheter sheath device.

FIG. 3D is a cross-sectional side view of the catheter sheath device of FIG. 3A, but with the different intravascular device of FIG. 3C being fully received into the catheter sheath device.

Figure 1A:
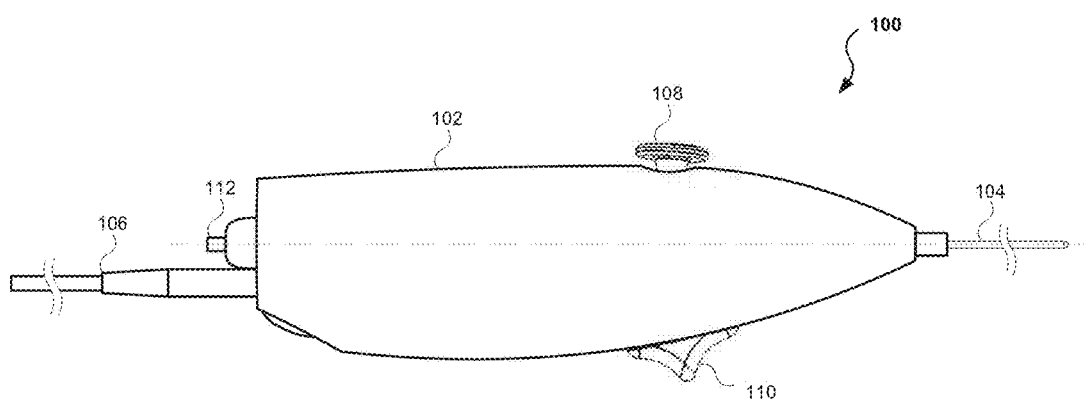
FIG. 1A is a diagrammatic side view of a catheter delivery system according to an embodiment of the present disclosure.

For clarity of discussion, elements having the same designation in the drawings may have the same or similar functions. The drawings may be better understood by referring to the following Detailed Description.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, and elliptical, etc.) or non-geometric cross-sectional profiles. Flexible elongate members include, for example, guidewires and catheters. In that regard, catheters may or may not include a lumen extending along its length for receiving and/or guiding other instruments. If the catheter includes a lumen, the lumen may be centered or offset with respect to the cross-sectional profile of the device.

In some embodiments, the flexible elongate members of the present disclosure contain one or more electronic, optical, or electro-optical components. For example, without limitation, a flexible elongate member may contain one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound, often referred to as intravascular ultrasound (IVUS) and intracardiac echocardiography (ICE), and optical coherence tomography (OCT). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of a flexible elongate member, containing one or more electronic, optical, and/or electro-optical components as described herein are between about 0.047" and about 0.053". As such, the flexible elongate members facilitating the placement of the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected", "coupled", and variations thereof as used herein include direct connections, such as being glued or otherwise fastened directly to, on, within, etc. another element, as well as indirect connections where one or more elements are disposed between the connected or coupled elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

FIG. 1A is a side view of a catheter delivery system 100 such as may be used during therapeutic or diagnostic procedures. The catheter delivery system 100 includes a housing 102, which may be formed from a rigid material, such as plastic or metal. Some embodiments of housing 102 are designed to be discarded after a surgical operation is performed, while other embodiments are sterilizable to permit reuse. As depicted, the housing 102 is formed to facilitate hand-held operation by a user, but some embodiments are not so shaped.

System housing 102 contains a variety of components that facilitate operation of the catheter delivery system 100. Such components may include motors, gearboxes, coupling gears, and/or other features to control the rotation of intravascular devices inserted into port 112. In some embodiments, rotation is performed manually rather than by the mechanized control. Some embodiments may also include one or more computer processors, memory, actuators, AC/DC converters, preamplifier circuitry for ultrasound and other signals, A/D and D/A converters, optical sensors and converters, filters, and/or other features to provide data processing and/or electronic control to the catheter delivery system and associated components, including in some instances the intravascular device(s) received by the catheter delivery system.

Cams, levers, gears, and/or other steering mechanisms are coupled to a steering actuator and/or a plurality of steering wires running through to a distal end of a catheter sheath device 104 in order to provide steering capabilities to the catheter delivery system 100 and, in particular, the distal portion of the catheter sheath device 104. In some embodiments, the steering mechanisms include stepper motors, linear motors, and/or servo actuators. The catheter sheath device 104 is a steerable catheter sheath as will be discussed in more detail later in this disclosure. In the depicted embodiment, the outer diameter of the catheter sheath 104 is between about 0.047" and about 0.053". The catheter 104 may have one or more lumens. For example, in the depicted embodiment the catheter sheath 104 includes a lumen with an inner diameter of about 0.017" to about 0.031". In other embodiments, other diameters may be used. For example, some embodiments of the catheter sheath 104 includes a larger lumen, with an inner diameter greater than 0.035" so as to be able to permit the passage of a wire approximately 0.035" in diameter.

The catheter delivery system 100 also includes a cable 106 to supply power to the variety of components inside housing 102 and/or catheter sheath device 104. In some embodiments, cable 106 further includes a communications wire to facilitate communication between the catheter delivery system 100 and a controller. In that regard, the controller is utilized in some instances to control operations of one or more components of the catheter delivery system 100 and/or an intravascular device delivered by the catheter delivery system.

Two steering mechanisms are coupled to the proximal ends of the steering wires inside housing 102. The top steering mechanism is a joystick 108, which can be moved forward, backward, left, right, and combinations thereof by a user's thumb. The steering wires are coupled to the joystick 108 so that, for example, moving the joystick 108 forward may move a distal portion of the catheter sheath device 104 down and moving the joystick 108 backward may move the distal portion of the catheter sheath device 104 up. Similarly, moving the joystick 108 to the right may move the distal portion of the catheter sheath device 104 to the left, and moving it to the left may move the distal portion to the right. In some embodiments, one or more of the movements of the distal portion in response to movements of the joystick 108 may be the opposite of those disclosed above. The thumb-controlled joystick 108 provides a controller arrangement that is similar to some video game and/or computer controllers. Accordingly, the steering functionality of the catheter delivery system 100 is presented in an interface that may be more familiar, and therefore more intuitive, to some users, especially younger generations of medical personnel.

The second of the two steering mechanisms is a trigger 110, which can be manipulated by the user's index and middle fingers. The trigger 110 provides a frictional force by spring pressure to the back of the steering mechanisms, thereby providing a "brake" functionality to the steering to allow the user to set and retain the steering in a given position. Actuating the trigger 110 proximally releases the friction and allows for manipulation of the joystick 108. Releasing the trigger 110 "locks" the steering and facilitates use of the central lumen without loss of position in tortuous vasculature.

The housing 102 includes a port 112, that is aligned with a central longitudinal axis of the catheter sheath device 104 such that therapeutic and/or diagnostic catheter devices and/or sensor cores can be inserted into port 112 and be guided to the distal end of the catheter sheath device 104. In FIG. 1, this common pathway is depicted by the dashed line running through port 112 and the catheter sheath 104.

Figure 1B:
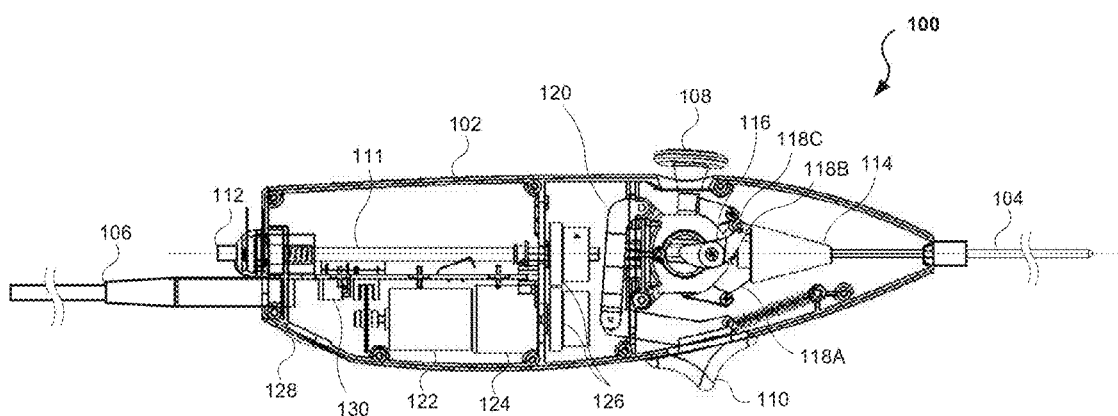
FIG. 1B is a diagrammatic partial cut-away side view of the catheter delivery system of FIG. 1A.

FIG. 1B is a partial cross-sectional side view of the catheter delivery system 100 as seen in FIG. 1A. The housing 102 of the catheter delivery system 100 is depicted in cross-section. As discussed above, housing 102 includes a port 112, which has an opening aligned internally with several features, including catheter sheath device 104. It is through port 112 that the intravascular sensors and devices implementing a variety of diagnostic and therapeutic components are inserted into and removed from a central lumen in catheter sheath device 104. As an example, port 112 permits an IVUS core to be inserted into a central lumen of the catheter sheath device 104 in such a way that the IVUS transmitter/receiver core is positioned within a distal portion of the catheter sheath device 104, while the distal portion is steered into a desired location. In this regard, the IVUS core can provide visualization of the anatomy to assist the user in guiding the distal top of the catheter sheath device 104 to the desired location. Further, port 112 also allows a pressure sensor core to be inserted through the central lumen of catheter sheath device 104 to the desired location after removal of the IVUS core.

To that end, the inserted device may be removed through the central lumen of the catheter sheath device 104 through which it has been inserted and removed through port 112. To ensure that the inserted sensor core/device reaches the central lumen of catheter sheath device 104, housing 102 contains an alignment tube 111 that is coupled to the port 112, in some instances. When an intravascular device is inserted through port 112 and through alignment tube 111, it is guided through an opening through a steering wire guide 114, and into a central lumen of the catheter sheath device 104.

The steering wire guide 114 directs a plurality of steering wires included in the catheter sheath device 104 to attachment sites such as cam 116. In embodiments of catheter delivery system 100, four steering wires 118A-D are connected through steering wire guide 114 to four attachment sites. The attachment sites may be cams coupled to a joystick 108 such that the cams and/or other control structure(s) move in response to the joystick 108. In that regard, the cams and/or other control structure(s) are integrally formed with and/or fixedly attached to a portion of joystick 108 in some implementations. The cams and/or other control structure(s) are coupled to the steering wires in catheter sheath device 104 such that the movement of the cams and/or other control structure(s) imparted by the joystick 108 control the steering wires 118A-D to steer a distal portion of the catheter sheath device 104. An additional cam 120 couples the joystick 108 to the trigger 110 so that it may be used as a braking device.

Housing 102 also contains a motor 122 connected to a gearbox 124, which can increase or decrease the turn ratio between the motor 122 and gears 126 to adjust a speed at which a core component or intravascular device inserted through port 112 into catheter sheath device 104 is rotated. The motor 122 can be actuated by a button 128 coupled through electronics 130 to motor 122. In some embodiments, electronics 130 acts as a controller, while in other embodiments electronics 130 may also provide signal processing as well.

For example, when a rotational IVUS or OCT catheter is inserted through port 112 and into the distal portion of catheter sheath device 104, the motor 122 couples to a section of the catheter received within the housing and causes rotation of at least a portion of the catheter resulting in rotation of an imaging element at the distal end of the IVUS or OCT catheter.

In some embodiments, mechanical coupling between rotating core components and/or sensor devices is accomplished mechanically through the use of indexed mating components, constructed such that one piece is affixed rigidly to the rotating shaft of the motor 122 while the other is affixed rigidly to the proximal end of imaging or sensing device to be inserted. In such an embodiment, the sensing device would be inserted distally through the catheter sheath device 104 until the indexed mating components of the two respective halves engaged, thereby providing a mechanism for torque transfer from the catheter sheath device 104 to the imaging device. Other suitable embodiments might include a frictional fit, a tapered fit, a magnetic retention, or a snap feature.

Signal coupling from catheter to inserted sensors could be accomplished electrically by a rotary transformer or optically with a fiber optic rotary joint (FORJ). The rotary transformer may be split such that one half is rigidly affixed to the catheter, and the opposing half, which can rotate, is attached to the inserted sensor. The insertion of the sensor distally through the device would bring the two halves in close proximity and enable signal transmission across the transformer as is common in rotational IVUS devices. One embodiment of an optical sensor would incorporate a FORJ at the proximal end of the sensor such that it slides axially into the proximal end of the catheter sheath device 104 until at full insertion the catheter would prevent rotational movement of the stationary half of the FORJ and align the stationary half of the FORJ such that the OCT signal beam was transmitted to an optical receiver in the catheter circuitry.

The catheter delivery system 100 may be used in the diagnosis and/or treatment of a wide variety of conditions within a patient, including within vasculature (e.g., arteries and veins, including renals and peripherals), structural heart, kidneys, brain, lymph nodes, and/or other anatomical regions of interest. The outer diameter of the catheter sheath device 104 is sized appropriately for the intended application and/or anatomical region of interest. Housing 102 and the components contained therein, as mentioned above, provide a hand-actuated steering unit capable of steering the distal portion or distal tip of the attached catheter sheath device 104. A doctor may use the catheter delivery system 100 with a diagnostic component, such as IVUS, positioned in the distal portion of the catheter sheath device 104, to guide the catheter sheath device 104 to a region of interest and locate and observe the site of a suspected lesion or other problem. The doctor can then remove the diagnostic component to insert a therapeutic component through port 112 into the catheter sheath device 104 to provide the desired treatment to the observed location without removing the catheter sheath device 104 from the region of interest.

FIG. 2A depicts a catheter sheath device 200 according to an embodiment of the present invention. Catheter sheath device 200 is utilized as catheter sheath device 104 of the catheter delivery system 100 in some embodiments. The catheter sheath device 200 includes a flexible elongate member 202 (shown in cross-section) that has a distal portion 204 and a proximal portion 206. The distal portion 204 includes an opening 208 in a tapered portion 210 located at a distal end of the distal portion 204 of the flexible elongate member 202. The opening 208 is in communication with a lumen extending the length of the catheter sheath device 200. Catheter sheath device 200 further includes a flexible elongate member 212 situated within the lumen of flexible elongate member 202. The flexible elongate member 212 also includes a central lumen extending along its length.

The catheter sheath device 200 has a steering ring 214 that is situated within the distal portion 204 of flexible elongate member 202. In the illustrated embodiment, the steering ring 214 is physically coupled to the flexible elongate member 212 by a coupling tube 216. In the depicted embodiment, the coupling tube 216 physically abuts the steering ring 214 at its distal end, and is positioned within a counterbore located at a distal end 218 of the flexible elongate member 212. In the depicted embodiment, the counterbore is about 0.118" deep.

Distal portion 204 of the catheter sheath device 200 is steerable by manipulating steering wires 220, 222, 224, and 226 (steering wire 226 is not explicitly depicted in FIG. 2A but it is located opposite steering wire 222 as shown in FIGS. 2B and 2C). Distal portions of the steering wires 220, 222, 224, and 226 are fixedly coupled to the steering ring 214 in some instances. The steering wires 220, 222, 224, and 226 are made of any suitable material that is of sufficient strength to withstand the pull forces, while at the same time flexible enough to bend with the flexible elongate member 202. Examples of suitable materials for the steering wires 220, 222, 224, and 226 are metal (e.g. stainless steel, nitinol or other titanium alloy), non-metal (e.g. aramid fiber such as Kevlar®), and/or other high tensile types of materials, including polyetheretherketone (PEEK). In some implementations, steering wires 220, 222, 224, and 226 run the length of flexible elongate member 202 and are coupled to the steering ring 214 at a distal end of the steering wires 220, 222, 224, and 226 and to a hand-operated steering unit of a catheter delivery system at the proximal end. An embodiment of such a catheter delivery system is depicted in FIG. 1. However, the steering wires 220, 222, 224, and 226 may be coupled to any type of steering controller, whether hand-held, manual, automated, or otherwise. For example, in some instances a steering controller arrangement as described in U.S. patent application Ser. No. 11/696,573, titled "ULTRASOUND CATHETER AND HAND-HELD DEVICE FOR MANIPULATING A TRANSDUCER ON THE CATHETER'S DISTAL END" and filed on Apr. 4, 2007, hereby incorporated by reference in its entirety, is utilized. Further, in some such instances, the steering controller arrangement described in U.S. patent application Ser. No. 11/696,573 is adapted for use within the housing 102 (or similar structure) that allows a core element or intravascular device to be advanced through the housing 102 and into a lumen of a sheath that is steered by the steering controller arrangement of the housing 102.

In the depicted embodiment, flexible elongate member 212 does not extend the full length of flexible elongate member 202, though in other embodiments it does. Rather, the distal portion 218 of flexible elongate member 212 is depicted as offset or spaced proximally from the distal end of flexible elongate member 202 by an amount at least the length of the coupling tube 216. The proximal end of the flexible elongate member 212 is offset or spaced distally from the proximal end of flexible elongate member 202. In some embodiments, flexible elongate member 212 is offset or spaced proximally from the steering ring 214 by a length, but not offset from the proximal end (i.e., proximal ends of the flexible elongate members 202 and 212 are coterminous).

In the depicted embodiment, the distal portion 204 of the flexible elongate member 202 bends more easily when coupling tube 216 and flexible elongate member 212 are made of materials of differing rigidities or have differing thicknesses of a single material. For example, the distal portion 204 may be more easily steered when the coupling tube 216 has a thinner material thickness than a thickness of the flexible elongate member 212. In some embodiments, the coupling tube 216 has an inner diameter of about 0.031", an outer diameter of about 0.038", and is about 0.438" long. Additionally, the distal portion 204 may be more easily steered when the coupling tube 216 is made from a less rigid material than the material from which flexible elongate member 212 is made. The length of the offset distance between flexible elongate member 212 and the steering ring 214 may also be adjusted to tailor the degree of motion exhibited by the distal portion 204.

In some embodiments, the flexible elongate member 212 is made from a softer material than the flexible elongate member 202. For example, the flexible elongate member 212 is formed using a 55 Shore D polyether block amide (PEBA) material, while the flexible elongate member 202 is a braid reinforced polyimide material. In such embodiments, the inner flexible elongate member 212 extends distally beyond the flexible elongate member 202 by about 0.375". Such embodiments are among the many embodiments of catheter sheath device 200.

FIG. 2A also includes two lines, 2B-2B and 2C-2C that indicate the location of the cross-sections depicted in FIGS. 2B and 2C, respectively. FIG. 2B depicts a planar cross-section taken along line 2B-2B in FIG. 2A, thus the cross-section of FIG. 2B is located in the distal portion 218 of flexible elongate member 212. As seen in FIG. 2B, catheter sheath device 200 includes a plurality of peripheral lumens. In the depicted embodiment, each of the plurality of peripheral lumens in oblong. In other embodiments, the peripheral lumens may have other shapes, such as circular or rectangular, and some peripheral lumens may have different shapes than others. The depicted embodiment includes eight peripheral lumens 230, 232, 234, 236, 238, 240, 242, and 244, but other embodiments may contain more or fewer peripheral lumens. The eight depicted peripheral lumens 230, 232, 234, 236, 238, 240, 242, and 244 are formed in the flexible elongate member 212, which also has a central lumen 246. The central lumen 246 is configured generally in the center of the flexible elongate member 212 and runs the entire length thereof.

In the illustrated embodiment, the peripheral lumens are about 0.008" in diameter with steering wires about 0.004" in diameter in them. The inner diameter of the central lumen 246 ranges from about 0.022" to more than 0.038", which is adequate to allow the passage of 0.035" guidewires. Other embodiments of the peripheral lumens may be as small as about 0.005". In some embodiments, larger peripheral lumens may be useful for conveying fluids such as contrast or administering drugs. In some embodiments, the central lumen 246 and/or peripheral lumens has a lubricious coating thereon.

In the catheter sheath device 200, four steering wires 220, 222, 224, and 226 are positioned within four of the plurality of peripheral lumens. As depicted, steering wire 220 runs within peripheral lumen 230, steering wire 222 runs within peripheral lumen 234, steering wire 224 runs within peripheral lumen 238, and steering wire 226 runs within peripheral lumen 242. Due in part to their positioning within the peripheral lumens and coupling to the steering ring 214, by manipulating the proximal ends of steering wires the distal portion 204 of flexible elongate member 202 (and any components positioned therein) may be steered in a desired direction. In some implementations, the steering wires 220, 222, 224, and 226 are coupled to the steering ring 214 in general alignment with lumens 230, 234, 238, and 242 in which they are received.

Additionally, by positioning the steering wires 220, 222, 224, and 226 inside the peripheral lumens, the central lumen 246 of flexible elongate member 212 may have increased capacity for the insertion, placement, positioning, and extraction of intravascular devices of various modalities through the central lumen 246. In the illustrated embodiment, an intravascular device 248 is shown position within the central lumen 246. Intravascular device 248 includes one or more electronic, optical, or electro-optical components in some implementations. Generally, the intravascular device 248 may be any type of intravascular device now known or developed in the future. As depicted, the intravascular device 248 substantially fills the space provided by central lumen 246, but with sufficient spacing to allow the intravascular device 248 to be advanced and/or retracted through the central lumen 246.

For example, intravascular device 248 may be diagnostic device inserted through the central lumen 246 into the distal portion 204 of the flexible elongate member 202. In some instances, the diagnostic device is received within the distal portion 204 of the flexible elongate member 202 while advancing and steering the distal portion 204 of the flexible elongate member 202 to a region of interest within the patient. To that end, data from the diagnostic device is utilized to guide placement of the flexible elongate member 202 in some instances. For example, in some implementations an imaging catheter is received within the flexible elongate member 202 such that images obtained by the imaging catheter can be utilized to guide the flexible elongate member to the desired location. Further, once positioned at the region of interest, the diagnostic core can be operated, either within the distal portion 204 of the flexible elongate member 202 or distally beyond the distal end of the flexible elongate member 202, to obtain data regarding the region of interest (e.g., images, pressure measurements, flow measurements, etc.).

After the region of interest has been monitored by the diagnostic core, the diagnostic core may be removed from the central lumen 246 without removing the catheter sheath device 200 from the region of interest inside the patient. Then, another device of a different modality may be inserted through the central lumen 246 into the distal portion 204 of the flexible elongate member 202, where it may be used to gather additional data and/or administer an associated therapy at the region of interest. For example, in some instances, the device of the second modality includes a treatment component (e.g., ablation element, balloon, stent, drug, etc.) that is used to treat a malady observed at the site previously by the use of diagnostic device. After the treatment with the treatment component has been completed, the treatment device may be removed from the flexible elongate member 202. Additional data may be gathered by reinserting the first device into the flexible elongate member 202 in order to evaluate the results of the treatment (e.g., by comparing the data from prior to the treatment to data obtained after the treatment). A similar approach may be utilized to advance multiple diagnostic and/or multiple treatment devices to the region of interest to gather multiple types of diagnostic data and/or provide multiple types or quantities of treatments. In this manner, a plurality of diagnostic and/or therapeutic modalities may be used sequentially at the region of interest, while the catheter delivery sheath device remains largely stationary so that the advances of the various devices to the region of interest is simplified and expedited.

FIG. 2C is a cross-sectional end view of the catheter sheath device 200 of FIG. 2A along line 2C-2C of FIG. 2C in the distal portion 218 of the flexible elongate member 212. FIG. 2C depicts many of the same features that are depicted in FIG. 2B. For example, FIG. 2C depicts the plurality of peripheral lumens 230, 232, 234, 236, 238, 240, 242, and 244 as well as the steering wires 220, 222, 224, and 226 therein. In addition to depicting flexible elongate members 202 and 212, FIG. 2C also includes a depiction of the coupling tube 216 in cross-section. The depicted portion of coupling tube 216 is shown as inserted into the counterbore formed in the distal end of flexible elongate member 212. In the depicted embodiment, the counterbore allows the flexible elongate member 212 and coupling tube 216 to be securely coupled together. The flexible elongate member 212 and the coupling tube 216 may be fixedly coupled together by an adhesive, press-fit connection, by ultrasonic welding or thermal blending.

The coupling tube 216 includes a lumen 250 that is substantially aligned with the lumen 246 of the flexible elongate member 212. In some embodiments, the coupling of the flexible elongate member 212 and the coupling tube 216 eliminates any substantial gap between the lumens 246 and 250 so that the lumens 246 and 250 define a generally continuous lumen, having a substantially consistent diameter, through which intravascular devices may be advanced and removed. Additionally, in the depicted embodiment, the wall thickness of coupling tube 216 is the same as the thickness of material removed from flexible elongate member 212 (or not molded) to define the counter bore so that the central lumens 246 and 250 maintain the consistent diameter. In other embodiments, the two thicknesses are not the same and/or the sizes of lumens 246 and 250 are not the same.

FIGS. 3A-D depict the catheter sheath device 200 of FIGS. 2A-C in various stages of use with intravascular devices of different modalities in accordance with the present disclosure. As depicted in FIG. 3A, an intravascular device 302 of a first modality is fully inserted into the center lumen running through the flexible elongate member 202, through the flexible elongate member 212, and through the coupling tube 216. In some embodiments, the intravascular device 302 does not protrude out through the opening 208 at the distal end of the tapered portion. However, a distal portion of the intravascular device 302 extends distally through the opening 208 and beyond the distal end of catheter sheath device 208 in the depicted embodiment. The intravascular device and the flexible elongate member 202 may be secured together by providing a short section of reduced diameter at the distal tip of the lumen of flexible elongate member 202, thereby creating a flange which would mate against an opposing flanged face on the intravascular device, thereby preventing overextension. Other methods which may be used in other embodiments include a piezoelectric ring around the lumen that would constrict onto the outer diameter of the device in response to current, a pressure vessel which would expand inwardly onto the device with the addition of fluid, or constriction by a wire coil.

In FIG. 3B, the intravascular device 302 is shown being removed from the central lumen 246 of the flexible elongate member 212 in catheter sheath device 200. The intravascular device 302 is removed through the port 112 as described in FIG. 1. In some instances, the removal of the intravascular device 302 is performed in order to provide space for an intravascular device 304 of a second modality.

In FIG. 3C, the intravascular device 302 has been completely removed from the central lumen 246 of the catheter sheath 200. In its place, the intravascular device 304 is depicted as being inserted into the central lumen. The modality of the intravascular device 304, in some embodiments, is a different modality than that of the intravascular device 302. For example, the intravascular device 302 may be a diagnostic device, while the intravascular device 304 may be a treatment device. While in other embodiments, both intravascular devices 302 are diagnostic devices of two distinct or different modalities (e.g., an IVUS device and a pressure-sensing device) or variations of a single modality (e.g., a 20 MHz IVUS device and a 40 MHz IVUS device).

In FIG. 3D, the intravascular device 304 is fully inserted through the central lumen 246 of the flexible elongate member 212 and central lumen 250 of coupling tube 216 until it is in a desired position for use. Again, as depicted, a portion of the intravascular device 304 protrudes through the opening 208 at the distal end of catheter sheath device 200. However, depending on the modality of the device, it may be contained wholly within the catheter sheath device 200.

Figure 4A:
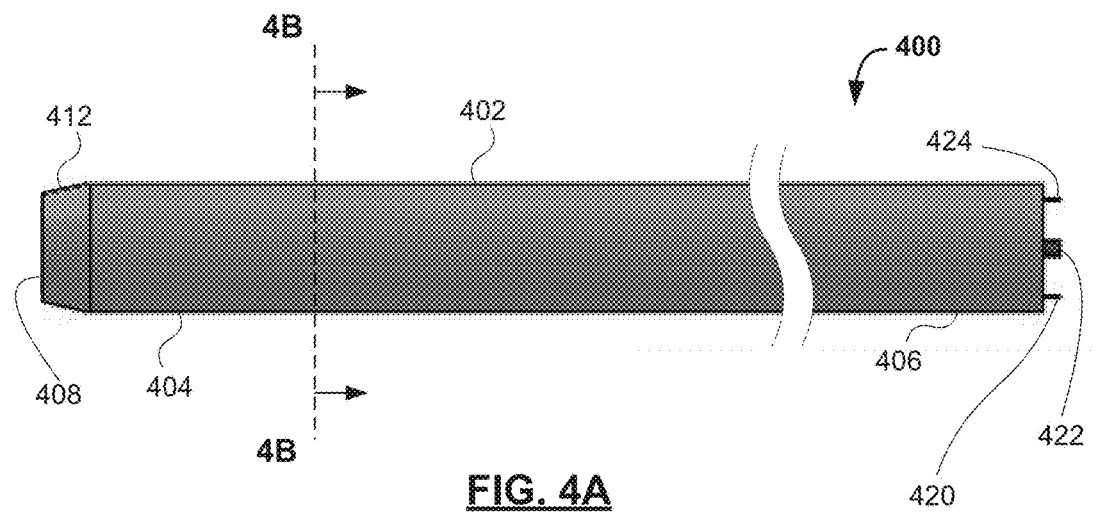
FIG. 4A is a side view of a portion of a catheter sheath device according to an embodiment of the present disclosure.

FIG. 4A depicts a side view of a catheter sheath device 400 according to another embodiment of the present disclosure. Catheter sheath device 400 is utilized as the catheter sheath device 104 of the catheter delivery system 100 in some embodiments. In many respects, catheter sheath device 400 is similar to the catheter sheath device 200 of FIGS. 2A-C, but instead of having two nested flexible elongate members, includes a single flexible elongate member. In particular, catheter sheath device 400 includes a flexible elongate member 402. Flexible elongate member 402 includes a distal portion 404 and a proximal portion 406. In the depicted embodiment, flexible elongate member 402 is made from polyimide. More generally, the flexible elongate member 402 may be made from a flexible biocompatible polymer or a polymer having a biocompatible coating thereon.

In the illustrated embodiment, the distal portion 404 includes an opening 408 at a distal end of the flexible elongate member 402. The opening 408 provides access for an intravascular device, or a part thereof, positioned within the distal portion 404 of the flexible elongate member 402 to be advanced distally beyond the flexible elongate member 402 to a region of interest within a patient. In some embodiments, the entire intravascular device is situated within a lumen 410 inside flexible elongate member 402. A tapered portion 412 at the distal end of the distal portion 404 is provided to facilitating steering within a patient without causing damage to surrounding anatomical structures.

The catheter sheath device 400 is a steerable catheter sheath. Thus, the distal portion 404 may be manipulated along two dimensions (e.g., in an x-y plane extending perpendicular to a longitudinal z-axis of the catheter sheath device), along with any intravascular device included therein. As depicted in FIG. 4A, these dimensions are (1) up and down and (2) in and out of the page (left, right, up, and down as viewed in FIG. 4B). Distal portion 404 of the catheter sheath device 400 is steerable by manipulating steering wires 420, 422, 424, and 426 (steering wire 426 is not explicitly depicted in FIG. 2A but it is located opposite steering wire 422). The steering wires 420, 422, 424, and 426 are made of any suitable material that is of sufficient strength to withstand the pull forces, while at the same time flexible enough to bend with the flexible elongate member 202. Examples of suitable materials for the steering wires 420, 422, 424, and 426 are metal (e.g., stainless steel, nitinol or other titanium alloy) or non-metal (e.g., aramid fiber such as Kevlar®) or other high tensile types of materials, including polyetheretherketone (PEEK). The steering wires run the length of flexible elongate member 402 and are coupled to a steering ring at a distal end of the steering wires and to a steering actuator, such as joystick 118 of the catheter delivery system 100 depicted in FIG. 1.

Figure 4B:
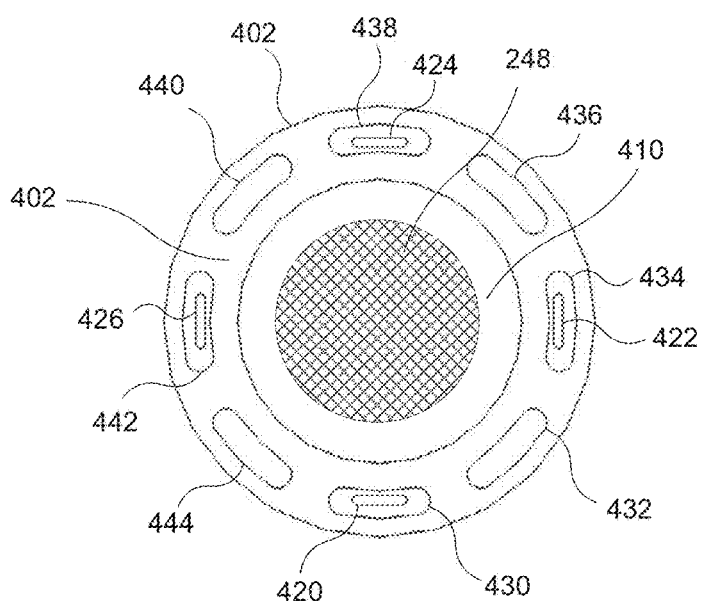
FIG. 4B is a cross-sectional end view of the catheter sheath device of FIG. 4A taken along line 4B-4B of FIG. 4A.

FIG. 4B presents a cross-sectional end view of the catheter sheath device 400 taken along line 4B-4B of FIG. 4A. The cross-section of FIG. 4B more clearly depicts the steering wires and how they are positioned within the flexible elongate member 402. Each of the four steering wires 420, 422, 424, and 426 is disposed within one of a plurality of peripheral lumens. The depicted embodiment includes a total of eight peripheral lumens 430, 432, 434, 436, 438, 440, 442, and 444, while other embodiments may include more or fewer. Steering wires 420 and 424 are disposed opposite each other in peripheral lumens 430 and 438, respectively. And steering wires 422 and 426 are disposed opposite each other in peripheral lumens 434 and 442, respectively. As shown, steering wires 420 and 424 control movement up and down, while steering wires 422 and 426 control movement left and right (as viewed in FIG. 4B).

As depicted, some of the peripheral lumens are empty. Specifically, peripheral lumens 432, 436, 440, and 444 are depicted as empty. However, in some embodiments, some or all of these peripheral lumens may contain one or more optical fibers and/or electrical conductors, which may be formed of any suitable conductive material including without limitation copper, copper alloys, silver, silver alloys, aluminum, glass and/or combinations thereof. In such embodiments, these communication and/or power lines run the length of the catheter sheath device 400, so that a component positioned in the distal portion 404 may be supplied with power, may receive signals from a controller, and/or send signals to the controller.

For example, in some embodiments, the distal portion 404 contains an array of ultrasound transducers (e.g., 8, 16, 32, 64, 128, or other number of transducer elements) having power supply lines and communication lines running from the distal portion through one or more of the peripheral lumens 432, 436, 440, and 444 of flexible elongate member 402 to a connector at the proximal end of the catheter sheath device 400. Generally, the array of ultrasound transducers are positioned adjacent the distal portion 404 of the catheter sheath device. In some instances, the transducers are positioned circumferentially around the diameter catheter sheath device at a position proximal of the tapered portion 412. In that regard, in some implementations the transducers are configured to emit ultrasound signals in a direction perpendicular to a longitudinal axis of the catheter sheath device 400 to provide side-looking functionality. In other instances, the transducers are positioned around the tapered portion 412 such that the transducers are mounted at an oblique angle with respect to the longitudinal axis of the catheter sheath device 400. In that regard, in some implementations the transducers are configured to emit ultrasound signals in a direction along the longitudinal axis of the catheter sheath device 400 and/or at an oblique angle to the longitudinal axis in order to provide forward-looking functionality and/or side-looking functionality. In this regard, in some instances the imaging data provided by the array of ultrasound transducers is utilized to guide the placement of the catheter sheath device 400 within a patient. Through wired and/or wireless communication, the connector associated with the array of ultrasound transducers is in communication with the controller. In some embodiments, the controller may have one or more computer processors, memory, and signal processing circuitry.

As seen in the cross-section of FIG. 4B, flexible elongate member 402 includes a central lumen 410 in addition to the peripheral lumens already mentioned. The central lumen 410 is of adequate size to allow for the insertion and positioning of an intravascular device in distal portion 404, after the catheter sheath device 400 has been positioned within a patient's body. At the location of the plane depicted by line 4B-4B, the central lumen 410 includes an intravascular device 248.

In some embodiments, the intravascular device 248 received within the distal portion 404 is an imaging device. In such embodiments, there may be one or more conductors running through the length of the intravascular device 248 to activate the ultrasound transducer or transducers and/or transmit echo signals received by the ultrasound transducer(s). Embodiments of intravascular device 248 may include both an electrical conductor for signal transmission and/or power supply and a structural support member, such as a drive cable or core wire, to permit positioning and manipulation of a component disposed at the distal end of intravascular device 248. For example, by manipulating the structural support member, the ultrasound transducer(s) may be controllably, rotatably directed inside flexible elongate member 402 by physically rotating the intravascular device 248 as a whole or just the structural support member and associated components. In some instances, a motor (such as motor 122 of FIG. 1B) is utilized to impart rotation to a proximal portion of the intravascular device 248 and/or structure support members thereof.

In some embodiments, an intravascular device 248 having a first modality, such as IVUS, may be removed from the central lumen 410 and a second intravascular device having a second modality, such as a pressure sensor, may be inserted through the central lumen 410 until it is positioned within the distal portion 404 (or a region of interest outside of the catheter sheath device 400) such that the different modalities may be used the gather data. The ability to exchange the intravascular devices while leaving the catheter sheath device 400 in place provides significant benefits to both users and patients. Time is saved and more data is gathered from the region of interest, giving a more comprehensive knowledge of the site for better evaluation and treatment. Additionally, the use of the first modality may provide a doctor with valuable information to use in the selection of a second, and/or a third modality. For instance, a first modality may be a diagnostic modality, such as FFR. A doctor may use the FFR system to diagnose a particular problem that can be treated with a certain treatment modality and then remove that FFR system from the catheter sheath device 400. The doctor may then insert an intravascular device of the desired second modality such as an ablation catheter, the tip of which may be used to remove material from arterial walls based on the data received from the FFR system.

Figure 5:
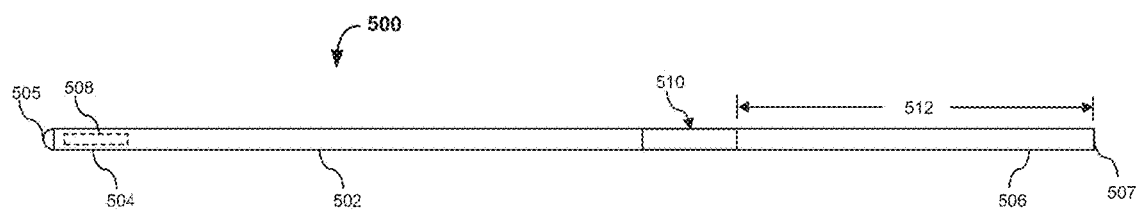
FIG. 5 is a diagrammatic side view of an intravascular device such as may be inserted into a catheter sheath device according to an embodiment of the present disclosure.

Referring now to FIG. 5, shown therein is a portion of a catheter device 500 according to an embodiment of the present disclosure. Embodiments of the catheter device 500 may be inserted and removed from the central lumens of embodiments of catheter sheath devices 200 and 400. In that regard, the catheter device 500 includes a flexible elongate member 502 having a distal portion 504 adjacent a distal end 505 and a proximal portion 506 adjacent a proximal end 507. A component 508 is positioned within the distal portion 504 of the flexible elongate member 502 proximal of the distal tip 505. Generally, the component 508 is representative of one or more electronic, optical, or electro-optical components. In that regard, the component 508 is a pressure sensor, a temperature sensor, an imaging element, an optical fiber, an ultrasound transducer, a reflector, a mirror, a prism, an ablation element, an RF electrode, a conductor, and/or combinations thereof. The specific type of component or combination of components can be selected based on an intended use of the catheter device. In some instances, the component 508 is positioned less than 10 cm, less than 5, or less than 3 cm from the distal tip 505. In other instances, a portion of component 508 may protrude beyond the distal tip 505. In some instances, the component 508 is positioned within a housing of the flexible elongate member 502. In that regard, the housing is a separate component secured to the flexible elongate member 502 in some instances. In other instances, the housing is integrally formed as a part of the flexible elongate member 502. In some instances, the catheter device 400 is a catheter or guide wire configured to perform one or more of intravascular ultrasound (IVUS) (rotational or phased array), virtual histology (VH), forward looking IVUS (FL-IVUS), intravascular photoacoustic (IVPA) imaging, pressure sensing, flow sensing, optical coherence tomography (OCT), computed tomography, intracardiac echocardiography (ICE), forward-looking ICE (FLICE), intravascular palpography, transesophageal ultrasound, and/or other suitable medical imaging, sensing, and/or diagnostic modalities capable of being incorporated into a catheter or guide wire.

The catheter device 500 also includes a connector 510 adjacent the proximal portion 506 of the device. In that regard, the connector 510 is spaced from the proximal end 507 of the flexible elongate member 502 by a distance 512. Generally, the distance 512 is between 0% and 50% of the total length of the flexible elongate member 502. While the total length of the flexible elongate member can be any length, in some embodiments the total length is between about 1300 mm and about 4000 mm, with some specific embodiments have a length of 1400 mm, 1900 mm, and 3000 mm. Accordingly, in some instances the connector 510 is positioned at the proximal end 507. In other instances, the connector 510 is spaced from the proximal end 507. For example, in some instances the connector 510 is spaced from the proximal end 507 between about 0 mm and about 1400 mm. In some specific embodiments, the connector 510 is spaced from the proximal end by a distance of 0 mm, 300 mm, and 1400 mm.

As noted above, in some instances the connector 510 provides a connection between the component 508 of the catheter device 500 and an external device. Accordingly, in some embodiments one or more electrical conductors, one or more optical pathways, and/or combinations thereof extend along the length of the flexible elongate member 502 between the connector 510 and the component 508 to facilitate communication between the connector 510 and the component 508. Generally, any number of electrical conductors, optical pathways, and/or combinations thereof can extend along the length of the flexible elongate member 502 between the connector 510 and the component 508. In some instances, between one and ten electrical conductors and/or optical pathways extend along the length of the flexible elongate member 502 between the connector 510 and the component 508.

Embodiments of the catheter device 500 can be inserted and removed from the catheter sheath devices described above. For example a first embodiment of catheter device 500 may include an imaging component. After the first embodiment of catheter device 500 has been used to image an area and/or guide the distal end of the catheter sheath device to a desired location, it is removed from the catheter sheath device and replaced with a second embodiment of catheter device 500. This second embodiment of catheter device 500 has a further diagnostic component and/or a treatment component that is advanced through the catheter sheath device and used at the same region of interest.

Figure 6:
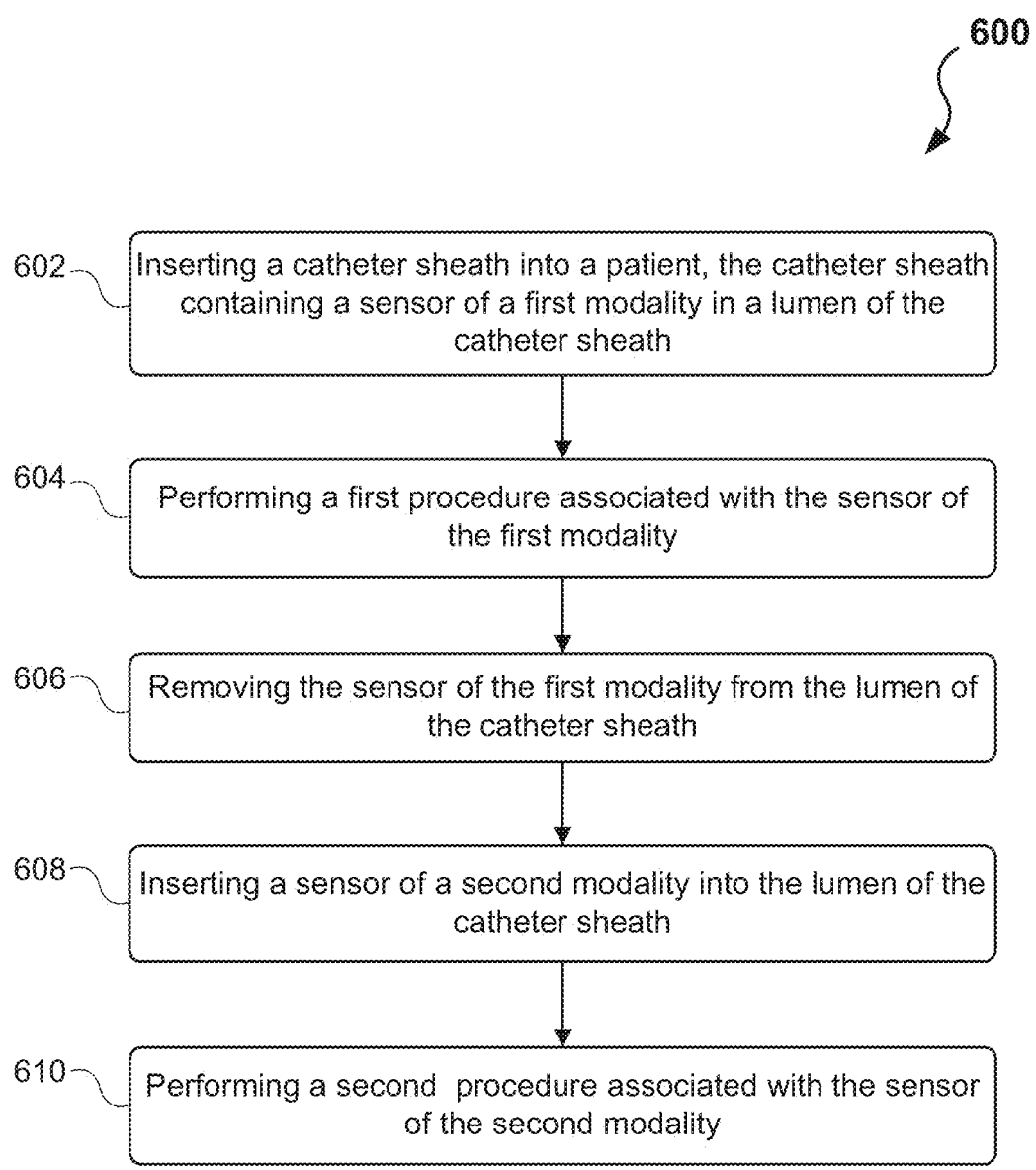
FIG. 6 is flow chart illustrating a method 600 for using a catheter delivery system according to an embodiment of the present disclosure.

FIG. 6 is flow chart of a method 600 for using a catheter delivery system to direct multiple modalities to a single region of interest in a patient. The modalities include any combination of diagnostic and/or treatment modalities, including but not limited to imaging (e.g., rotational ultrasound imaging, phased-array ultrasound imaging, OCT imaging, thermal imaging, spectroscopy, infrared, near-infrared, and/or combinations thereof), pressure sensing (e.g., piezoresistive, capacitive, piezoelectric, and/or combinations thereof), flow sensing (e.g., Doppler ultrasound, pressure, and/or combinations thereof), ablation (e.g., ultrasound ablation, laser ablation, thermal ablation, RF ablation, and/or combinations thereof), implants (e.g., stent, filter, valve, and/or combinations thereof), balloons, drugs, and/or any other suitable modalities.

Method 600 as described below includes a plurality of steps. It is understood that additional steps can be provided before, during, and after the steps of method 600, and some of the steps described can be replaced or eliminated for other embodiments of the method. At step 602, a doctor or technician inserts a steerable catheter sheath of a delivery system into a patient. The steerable catheter sheath may have a component of a first modality received within a lumen of the sheath during insertion. In some instances, the component of the first modality received within the lumen of the sheath is utilized to guide the sheath during insertion. For example, imaging data and/or pressure data received from the component may be utilized to guide placement, including steering, of the distal tip of the sheath in some instances. At step 604, the doctor performs a first procedure associated with the component of the first modality. The component associated with the first modality is removed from the lumen of the sheath in step 606. At step 608, a component of a second modality is inserted into the lumen in step 608 after the component of the first modality is removed. In step 610, the doctor or technician performs a second procedure associated with the component of the second modality. Exemplary procedures include gathering imaging data, flow data, pressure data, and other kinds of data and also performing treatments of various kinds.

Method 600 of FIG. 6 may be better understood with reference to the earlier figures. For example, the catheter delivery system 100 may be used by a doctor to introduce a catheter sheath device 104 (having the features of any of the catheter sheath devices described above) into a patient (step 602). Catheter sheath device 104 includes a steerable flexible elongate member. At the time of insertion, the catheter sheath device 104 may or may not contain a catheter 500 of FIG. 5, such as a catheter having an imaging sensor so that the doctor may observe the placement of the catheter that is being steered to a location of interest and to observe the location of interest (step 604). In some instances, the imaging sensor provides forward-looking, side-looking, and/or combinations thereof. Mechanical and electrical or optical couplings connect the catheter to a housing like housing 102. For devices which have no direct interface with the housing 102. A Luer fitting at the proximal end of the housing 102 may allow the addition of a common rotating hemostasis valve (RHV), which can provide axial location through constriction as the valve is closed on the device passing through it.

Using the information obtained from the imaging sensor, the doctor may determine that another form of data may be usefully gathered at the region of interest and/or that a particular treatment is needed. The catheter device having the imaging sensor is then removed from the central lumen of the sheath (step 606). The doctor may determine that a pressure sensor should be used to gather pressure data at the site for making FFR determinations. The pressure sensor, which may be part of another catheter device, is fed through port 112 into the central lumen of catheter sheath device 104 until the pressure sensor is positioned in the distal portion (step 608). Once the pressure sensor is in position, the doctor may gather data using the pressure sensor (step 610).

Many other examples may be offered of using two or more different modalities to gather data and/or apply a therapy to a site by removing and replacing a catheter device of one modality with a catheter device of another modality.

The examples provided above are exemplary only and are not intended to be limiting. One skilled in the art may readily devise other systems consistent with the disclosed embodiments which are intended to be within the scope of this disclosure. As such, the application is limited only by the following claims.

What is claimed is:

1. A method for directing multiple intravascular devices to a region of interest within a vessel of a patient, the method comprising:
    inserting a catheter sheath including a flexible elongate member having a central lumen situated within the catheter sheath into the patient;
    guiding a steerable distal portion of the catheter sheath to the region of interest utilizing a steering actuator coupled to a steering ring situated within a distal portion of the catheter sheath encircling the central lumen, wherein the steering ring is coupled to a distal end of the flexible elongate member via a coupling tube situated within the catheter sheath so that a proximal side of the coupling tube is positioned within a counterbore formed in the distal end of the flexible elongate member and extends the central lumen and a distal end of the coupling tube abuts a proximal side of the steering ring, the flexible elongate member being spaced proximally from the steering ring by the coupling tube;
    performing a first procedure at the region of interest with a first intravascular device extending into the central lumen of the catheter sheath at least partially received within the distal portion of the catheter sheath distal to the steering ring; and
    performing a second procedure at the region of interest with a second intravascular device at least partially received within the distal portion of the catheter sheath, the second procedure being a different modality than the first procedure.

2. The method of claim 1, further comprising: inserting the first intravascular device into a lumen of the catheter sheath after the catheter sheath has been inserted into the patient.

3. The method of claim 1, further comprising: inserting the first intravascular device into a lumen of the catheter sheath prior to guiding the distal portion of the catheter sheath to the region of interest.

4. The method of claim 3, wherein data obtained from the first intravascular device is utilized in guiding the distal portion of the catheter sheath to the region of interest.

5. The method of claim 4, wherein the data obtained from the first intravascular device is at least one of imaging data, pressure data, and flow data.

6. The method of claim 1, wherein imaging data from an array of ultrasound transducers at the end of the catheter sheath is utilized in guiding the distal portion of the catheter sheath to the region of interest.

7. The method of claim 1, further comprising:
    removing the first intravascular device from the catheter sheath; and
    inserting the second intravascular device into the catheter sheath;
    wherein the distal portion of the catheter sheath is maintained at the region of interest during the removal of the first intravascular device and insertion of the second intravascular device.

8. The method of claim 1, wherein the catheter sheath comprises:
    a plurality of peripheral lumens formed within the first flexible elongate member; and
    a plurality of steering lines extending within at least some of the plurality of peripheral lumens to the steering ring at the distal end of the flexible elongate member.

9. The method of claim 8, wherein a proximal section of each of the plurality of steering lines is coupled to a steering actuator.

10. The method of claim 9, wherein the steering actuator comprises a joystick coupled to a housing sized and shaped for handheld use by a user.

11. The method of claim 10, wherein the joystick is positioned on the housing for control by the user's thumb.

12. The method of claim 11, wherein a trigger mechanism is coupled to the housing opposite the joystick, the trigger mechanism configured to engage with the joystick to prevent the joystick from moving.

13. The method of claim 8, wherein the coupling tube is less rigid than the flexible elongate member to permit steering of the distal portion of the catheter sheath in response to manipulation of the steering lines.

14. The method according to claim 8, wherein the coupling tube and the catheter sheath form an annular space therebetween and the plurality of peripheral lumens terminate at the annular space and the plurality of steering lines pass therethrough.

15. A catheter delivery system comprising:
    a catheter sheath having a steerable distal portion including a steering ring and a coupling tube situated within the catheter sheath and a plurality of steering lines running through a plurality of peripheral lumens of a first flexible elongate member having a central lumen situated within the catheter sheath, the distal ends of the plurality of steering lines being connected to the steering ring in the steerable distal portion of the catheter sheath encircling the central and the proximal ends of the plurality of steering lines being connected to a steering actuator coupled to a housing sized and shaped for handheld use,
    wherein the coupling tube having a proximal end positioned within a counterbore formed in a distal end of the first flexible elongate member for extending the central lumen through the steerable distal portion and a distal end that abuts a proximal side of the steering ring such that the coupling tube proximally spaces the flexible elongate member from the steering ring, and wherein the housing includes an opening extending therethrough in communication with the central lumen to allow insertion of intravascular devices of different modalities into the central lumen and removal of the intravascular devices of different modalities from the central lumen, wherein the intravascular devices inserted into the central lumen extend at least partially distal to the steering ring encircling the central lumen.

16. The catheter delivery system of claim 15, further comprising a second flexible elongate member having a central lumen, the first flexible elongate member being positioned within the central lumen of the second flexible elongate member.

17. The catheter delivery system of claim 15, wherein the steering actuator comprises a joystick.

18. The catheter delivery system of claim 17, wherein the steering actuator further comprises a plurality of cams coupled to the joystick steering actuator.

19. The catheter delivery system of claim 18, wherein the joystick is positioned on the housing for control by the user's thumb.

20. The catheter delivery system of claim 19, wherein a trigger is coupled to the housing opposite the joystick, the trigger configured to prevent the joystick from moving when engaged with the joystick.

21. The catheter delivery system of claim 15, wherein the first flexible elongate member includes an opening at its distal end in communication with the central lumen such that the intravascular devices of different modalities can be advanced distally beyond the distal end of the first flexible elongate member through the opening.

22. The catheter delivery system of claim 15, further comprising at least one rotational actuator positioned within the housing, the rotational actuator configured to rotate at least a portion of an intravascular device passing through the housing and into the central lumen of the first flexible elongate member.

23. The catheter delivery system of claim 22, wherein the rotational actuator comprises a motor.

24. The catheter delivery system of claim 22, wherein the rotational actuator is configured to impart rotation to a drive shaft of the intravascular device passing through the housing and into the central lumen of the first flexible elongate member.

25. The catheter delivery system of claim 15 wherein the proximal end of the coupling tube is positioned within a counterbore located at the distal end of the first flexible elongate member, and wherein the coupling tube is less rigid than the first flexible elongate member to permit steering of the distal portion of the catheter sheath in response to manipulation of the steering lines by the steering actuator.

26. The catheter delivery system of claim 15, further comprising an annular space formed between the coupling tube and the catheter sheath, wherein the plurality of peripheral lumens terminate at the annular space and the plurality of steering lines pass therethrough.

27. A catheter delivery system comprising:
a housing, the housing including a joystick; and
a catheter sheath having a central lumen defined by a first flexible member situated therein, the catheter sheath having a steerable distal portion including a coupling tube and a steering ring situated therein and a plurality of steering lines connected to the joystick at a proximal end and to the steering ring at a distal end, the steering ring being positioned within the steerable distal portion encircling the central lumen to allow an intravascular devices inserted into the central lumen to extend at least partially beyond the steering ring for application of a procedure by the intravascular device, wherein the catheter sheath further comprises a coupling tube having a proximal end positioned within a counterbore formed in a distal end of the first flexible member and a distal end of the coupling tube that abuts a proximal end of the steering ring such that the coupling tube proximally spaces the flexible elongate member from the steering ring and extends the central lumen through the steerable distal portion.

28. The catheter delivery system of claim 27 wherein the coupling tube is positioned within a counterbore located at the distal end of the catheter sheath, and wherein the coupling tube is less rigid than the catheter sheath to permit steering of the distal portion of the catheter sheath in response to manipulation of the steering lines by the joystick.

29. The catheter delivery system of claim 27 wherein the coupling tube is less rigid than the catheter sheath to permit steering of the distal portion of the catheter sheath in response to manipulation of the steering lines by the joystick.

30. The catheter delivery system of claim 27, further comprising an annular space formed between the coupling tube and the catheter sheath, wherein the plurality of peripheral lumens terminate at the annular space and the plurality of steering lines pass therethrough.

* * * * *